US007456026B2

(12) United States Patent
Janka et al.

(10) Patent No.: US 7,456,026 B2
(45) Date of Patent: Nov. 25, 2008

(54) IMAGING FLUORESCENCE CORRELATION SPECTROSCOPY FOR ANALYSIS OF MOLECULAR INTERACTIONS IN LOW VOLUMES

(75) Inventors: Reinhard Janka, Jena (DE); Volker Juengel, Jena (DE); Tilo Jankowski, Gueterfelde (DE); Frank Hecht, Weimar (DE)

(73) Assignee: Carl Zeiss MicroImaging GmbH, Jena (DE)

( * ) Notice: Subject to any disclaimer, the term of this patent is extended or adjusted under 35 U.S.C. 154(b) by 888 days.

(21) Appl. No.: 10/009,287

(22) PCT Filed: Feb. 15, 2001

(86) PCT No.: PCT/EP01/01663

§ 371 (c)(1),
(2), (4) Date: Nov. 6, 2001

(87) PCT Pub. No.: WO01/63259

PCT Pub. Date: Aug. 30, 2001

(65) Prior Publication Data

US 2005/0271549 A1  Dec. 8, 2005

(30) Foreign Application Priority Data

Feb. 22, 2000  (DE) ............................. 100 08 594

(51) Int. Cl.
*G01N 21/76* (2006.01)
*G01N 21/64* (2006.01)

(52) U.S. Cl. .................................. 436/172; 422/82.08

(58) Field of Classification Search ........................ None
See application file for complete search history.

(56) References Cited

U.S. PATENT DOCUMENTS 5,079,169 A   1/1992  Chu et al.

FOREIGN PATENT DOCUMENTS

| DE | 195 33 092 | 3/1997 |
| DE | 196 49 605 | 6/1998 |
| DE | 197 02 914 | 9/1998 |
| DE | 197 57 740 | 7/1999 |
| DE | 198 40 489 | 3/2000 |
| WO | WO 94/16313 | 7/1994 |

OTHER PUBLICATIONS

Weisshart et al. "The LSM 510 META—ConfoCor 2 system: An integrated imaging and Spectroscopic platform for single-molecule detection", Current Pharmaceutical Biotechnology (2004), 5(2), 135-154.*

(Continued)

*Primary Examiner*—Yelena G Gakh
(74) *Attorney, Agent, or Firm*—Reed Smith LLP

(57) ABSTRACT

An arrangement for the detection of fluorescent light with at least one imaging microscope unit and at least one device component for analyzing molecular interactions in small volumes, wherein measurement locations for the analysis of molecular interaction are determined and selected in at least two dimensions by the imaging method; the imaging microscope unit and the device components are operated with a shared control unit; and at least the analysis results of the device component are graphically depicted via the control unit and a computer.

8 Claims, 2 Drawing Sheets

OTHER PUBLICATIONS

"Counting Single Chromophore Molecules for Ultrasensitive Analysis and Separations on Microchip Devices" Julius C. Fister, et al. (Anal.Chem 1998, 70, 431-437).

Quantitative Fluorescence Confocal Laser Scanning Microscopy (CLSM) David R. Sandison, et al. (Handbook of Biological Confocal Microscopy, 1995 , 39.

XP-001005601 "Three-Dimensional Fluorescence Microscopy in Two-Photon Excitation Regime" Diaspro, et al.

XP-001005572 "Dynamic image correlation spectroscopy (ICS) and two-color image cross-correlation spectroscopy (ICCS): concepts and application" Wiseman, et al.

XP-000202077 "Analysis of confocal laser-microscope optics for 3-D fluorescence correlation spectroscopy" Qian, et al.

XP-001000182 "Quantitation of Membrane Receptor Distributions by Image Correlation Spectroscopy: Concept and Application" Petersen, et al.

S. Hunklinger, Confocal Fluorescence- Correlation- Spectroscopy for the Measurement of Diffussion Coefficients, Apr. 12, 1996, This diploma thesis was presented to the Substitute for Applied Physics.

Dirk Zuber Microscopy in Research and Practice, copyright 1995 by Git Verlag GmbH.

Koppel et al, Scanning Concentration Correlation Spectroscopy Using the Confocal Laser Microscope, Biophysical Journal, vol. 66 Feb. 1994, pp. 502-507.

Meseth, et al. Resolution of Fluorescence Correlation Measurements Biophysical Journal vol. 76 Mar. 1999, 1619-1631.

Schwille, et al. Molecular Dynamics in Living Cells Observed by Fluorescence Correlation Spectroscopy with One-and Two-Photon Excitation Biophysical Journal vol. 77 Oct. 1999 pp. 2251-2265.

Schwille, et al. Kinetic Investigations by Fluorescene Correlation Spectroscopy: The Analytical and Diagnostic Potential of Diffusion Studies Biophysical Chemistry, vol. 66 (1997) pp. 211-228.

Schwille, et al. Fluorescence Correlation Spectroscopy with Single-Molecule Sensitivity on Cell and Model Membranes Cytometry 36:176-182 (1999).

Walter, et al. Fluorescence Correlation Analysis of Probe Diffusion Simplifies Quantitative Pathogen Detection by PCR, Proc. Natl. Acad. Sci. USA, vol. 93, pp. 12805-12810 Nov. 1996, Biochemistry.

Klaus Dorre, et al. Techniques for Single Molecule Sequencing, Bioimaging 5 (1997), pp. 139-152.

Manfred Eigen, et al. Sorting Single Molecules: Application to Diagnostics and Evolutionary Buitechnology Proc. Natl. Acad. Sci. US, vol. 91, pp. 5740-5747 Jun. 1994.

Niles O. Petersen, et al. Quantitation of Membrane Receptor Distributions by Image Correlation Spectroscopy: Concept and Application, Biophysical Journal vol. 65 Sep. 1993 pp. 1135-1146.

ConfoCor 2—Fluorescence Correlation Microscope, Microscopy from Carl Zeiss (Brochure), Mar. 2000.

LSM 510—ConfoCor 2 Combination System (Manual), Sep. 2000.

* cited by examiner

IMAGING FLUORESCENCE CORRELATION SPECTROSCOPY FOR ANALYSIS OF MOLECULAR INTERACTIONS IN LOW VOLUMES

CROSS-REFERENCE TO RELATED APPLICATIONS

This application claims priority of International Application No. PCT/EP01/01663, filed Feb. 15, 2001 and German Application No. 100 08 594.6, filed Feb. 22, 2000, the complete disclosures of which are hereby incorporated by reference.

BACKGROUND OF THE INVENTION

Fluorescence correlation spectroscopy (FCS) implemented in a microscope construction (FCM) has proven successful for investigating biomolecular interactions particularly where the investigations are carried out in very small ranges of concentration of less than 1 µmol and in measurement volumes of less than $10^{-14}$ l. The measurement location plays only a minor role, provided the specimens to be examined are homogeneous. However, in connection with structured specimens such as biological cells, knowledge and selection of the measurement location is critically important. Formerly, this knowledge of the measurement location was gained by conventional transmitted-light and incident-light microscopy. For this purpose, switching was carried out between the FCS detection unit and a conventional fluorescence microscope arrangement. The use of conventional microscopy has several disadvantages. On the one hand, the specimens are exposed to high radiation loading; on the other hand, the optimal measurement location can not be localized in three-dimensional coordinate systems with the required accuracy of less than 1 µm.

The arrangements and methods described and claimed below, with reference to the drawings, advantageously make it possible to expand the FCS method to an imaging method (S-FCM). In this way, information can be gained concerning the spatial distribution of the molecular interactions under investigation.

DESCRIPTION OF THE PREFERRED EMBODIMENTS

Figure 1:
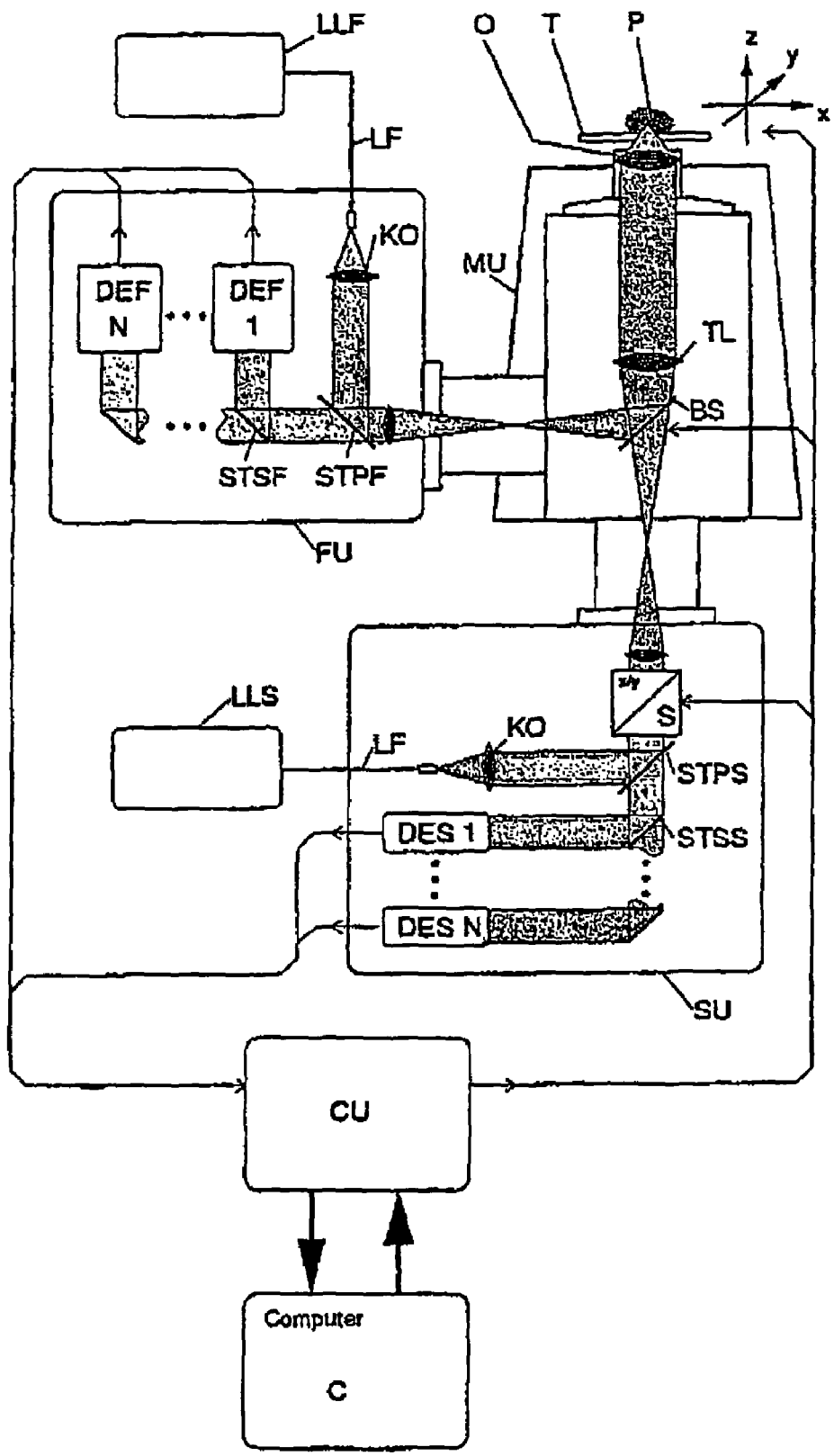
FIG. 1 is a schematic block diagram of an embodiment of the invention.

FIG. 1 shows a first advantageous arrangement. With a microscope unit MU (in this case, an inverted microscope for observing a specimen P via an objective O arranged below the specimen and a tube lens TL, the specimen P being located on a table T which is displaceable in x-, y- and z-direction), light from a laser light source LLS with one or more wavelengths is focused by a scanning unit SU in a specimen either directly or through a light-conducting fiber LF via collimating optics KO and a primary beam splitter STPS. The scanner S allows the light beam to be deflected in x-direction and y-direction; different specimen layers can be detected through vertical adjustment of the specimen table T or of objective O. The light coming from the specimen passes through the scanner S again and is assigned to detection channels DES1 . . . N by means of the secondary beam splitter STSS 1 . . . N and converted into electrical signals for evaluation via a control unit CU in a computer. The measured signals are used to obtain image information. By means of a beam switching unit BS, e.g., of a fully reflecting mirror or partially transmitting mirror which can be swiveled in and out, light LLF from a laser light source with one or more wavelengths is focused in the specimen by means of an FCS unit FU via a primary beam splitter STPF.

The light sources LLS and LLF may also be identical and can be coupled into the units SU and FU by suitable deflecting and switching elements. The fluorescent light coming from the specimen is directed through secondary beam splitters STSF 1 . . . N into one or more FCS detection channels DEF 1 . . . N and, for purposes of evaluation, converted into electrical signals and sent to the control unit CU. The signals are used for FCS analysis.

Autocorrelation analyses or cross-correlation analyses can be carried out depending on the detection channels that are installed. In this connection, for example, diffusion times, particle numbers, lifetimes and proportions of components are determined at the installed detection channels.

Data acquisition is controlled for both detection units by the same control unit CU and a computer C with a suitable program. Control of the specimen table T, vertical adjustment of the objective O and beam switching unit BS is also carried out by this computer-controlled control unit. Accordingly, as a result of integrating an FCS detection unit in a confocal laser scanning microscope system, it is also possible to combine FCS analysis results of measurements at various specimen locations to form images. This results in an advantageous arrangement which is suitable for determining FCS measurement locations with great accuracy while protecting the specimen and also for using FCS analysis results of measurements at different locations for generating images.

It is advantageously possible, for example, to use different colors to generate a color two-dimensional or three-dimensional depiction of diffusion times or other analysis results, depending on the measurement location.

Further, through the use of storage allocation, the recorded FCS image can be combined graphically, e.g., as an added color, with LSM images of different colors per channel.

FCS/LSM differentiating elements or quotient-forming elements or other combinations can also be formed and represented.

Modification, according to the invention, of the laser scanning microscope and operative combination with the FCS device unit are carried out by suitable programs in the computer by means of a device control unit shared by all of the components. The scanning unit, FCS unit, microscope unit and specimen position system are mechanically, optically and electronically adapted to one another and combined.

After the specimen is scanned, image points can be marked, brought into the measurement position for the FCS unit and measured.

The relevant points can be selected automatically according to given criteria (e.g., raster, structure detection of the image) or by the user according to individual assessment of the image recorded by the scanning unit.

The suggested construction makes possible a deliberate selection of microscopically small measurement locations in the specimen to be investigated by the FCS method. Further, it is possible to graphically detect and depict the spatial variation of the FCS analysis results from a systematic sequence of FCS measurements images and to correlate them with the LSM image.

Figure 2:
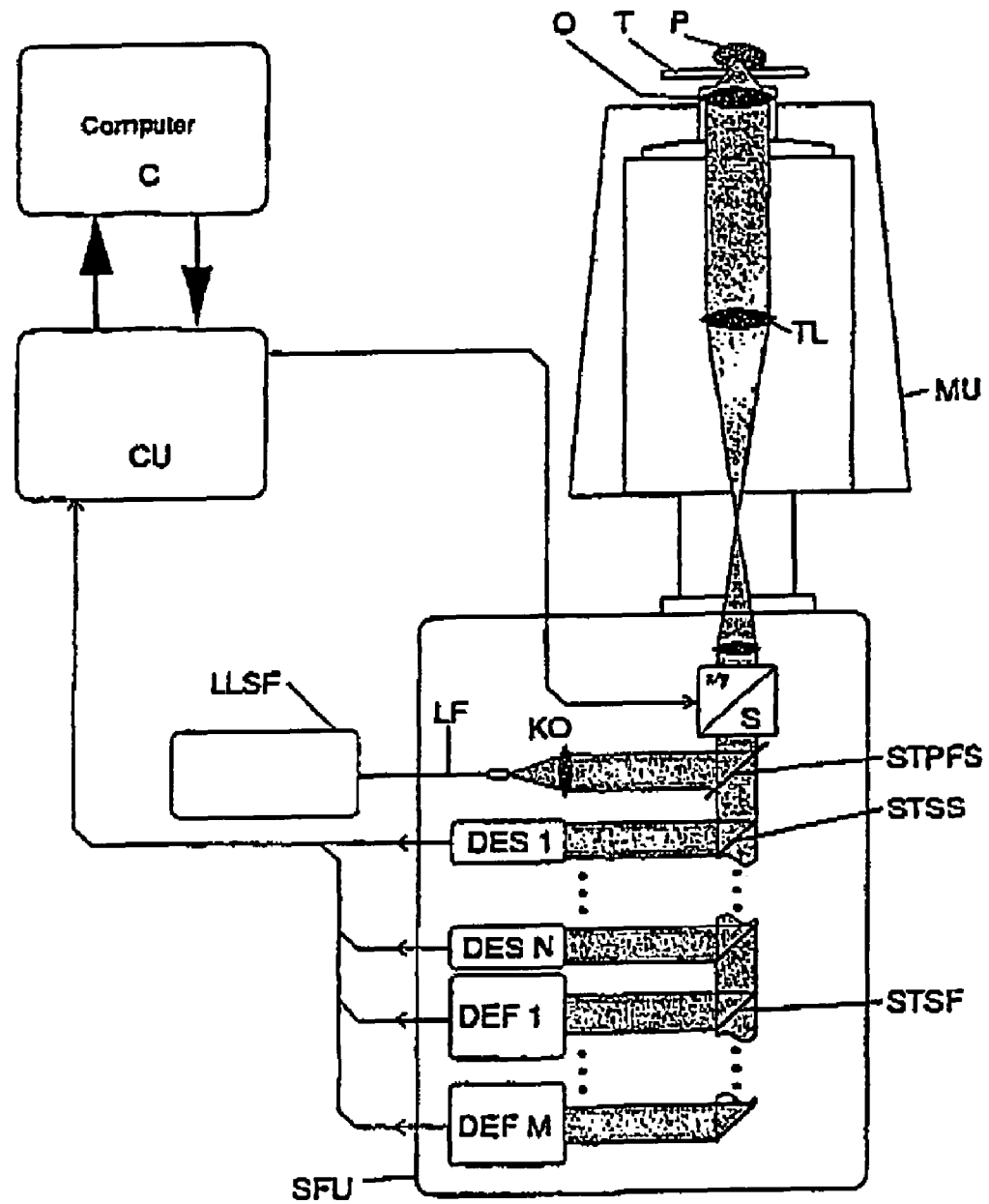
FIG. 2 is a further embodiment of the invention in schematic block representation.

FIG. 2 shows another advantageous arrangement. In this case, a shared laser unit LLSF and a shared primary beam splitter STPFS are provided in or at a shared unit SFU. Separate beam splitters and detectors DEF, STSF and DES, STSS are shown for LSM detection and FCS detection. The detectors DEF and DES can advantageously be identically constructed. The measurement mode and evaluating mode can be selected by means of the control unit CU. The common localization of the LSM and FCS detection channels in one unit results in an advantageous arrangement. As in the construction which was described with reference to FIG. 1, laser light of one or more wavelengths is focused through a scanning unit in the specimen by means of collimating optics and the primary beam splitter. A special advantage of this construction is that the measurement location for FCS measurement can also be selected by means of the scanner. In particular, it is possible in this way to advantageously expand the FCS analysis method to an imaging method (scanning FCM: S-FCSM). Reflected light and fluorescent light are captured by the objective, pass again through the scanner and are deflected by one or more secondary beam splitters into one or more LSM detection channels or FCS detection channels. Separation can then be carried out according to spectral characteristics or polarization characteristics. The detected light induces electrical signals which are directed to the control unit connected to the computer, including a suitable program, and are used in the latter for FCS analysis or image reconstruction.

In this case, the laser scanning microscope is modified in such a way that it contains components and evaluating procedures which also make it possible to carry out FCS measurements. Scan components and FCS components are combined, according to the invention, in such a way that beam splitting or beam switching such as is shown in FIG. 1 can be dispensed with. The advantage of this arrangement consists in that no specimen movements are necessary for carrying out the FCS analyses at the previously selected points because the measurement location can be adjusted by means of the scanner and through vertical adjustment of the objective.

The effective connection of the operating modes is carried out in that either the scanner is stopped directly during the scanning process and an FCS evaluation is carried out at the specimen points set in this way or, after the scanning process, an FCS evaluation is carried out by adjusting the mirrors or displacing the table while the scanner mirrors are stopped at determined points. The arrangement according to FIG. 2 enables FCS measurements with high positioning accuracy in quick succession. This suggested construction comprises a scanning fluorescence correlation microscope (S-FCM) which can show structural as well as biochemical information in images according to the invention.

While the foregoing description and drawings represent the present invention, it will be obvious to those skilled in the art that various changes may be made therein without departing from the true spirit and scope of the present invention.

What is claimed is:

1. An arrangement for the detection of fluorescent light comprising:
    at least one image-generating laser scanning microscope (LSM) unit for determining and selecting measurement locations for an analysis of molecular interaction, wherein measurement locations are scanned point to point in at least two dimensions;
    a fluorescence correlation spectroscopy (FCS) device unit for analyzing the molecular interactions in small volumes;
    a shared control unit for operating the at least one LSM unit and the FCS device unit; and
    a computer for graphically depicting results from analyzing the molecular interactions in small volumes;
    wherein the FCS device unit provides data and analysis based on a correlation with the image of the at least one LSM unit.

2. The arrangement according to claim 1, further comprising a movable specimen table and/or vertical adjustment of the objective for the selection of the specimen location for FCS measurement.

3. The arrangement according to claim 1, wherein a scanner of said LSM unit manually or automatically carries out said selection of measurement locations.

4. The arrangement according to claim 1, wherein fluorescent light from the sample is detected via at least one detector.

5. The arrangement according to claim 1, wherein detectors for detecting FCS signals are arranged following the scanner of the LSM in the detection direction.

6. A method of imaging fluorescence correlation spectroscopy for analysis of molecular interactions in low volumes, comprising the steps of:
    scanning the specimen by focusing illumination light from point to point in at least two dimensions by at least one image-generating laser scanning microscope (LSM);
    carrying out Fluorescence Correlation Spectroscopy (FCS) evaluation during the scanning process and/or after the scanning process for at least one specimen point by FCS device unit, using a shared control unit for simultaneous operation of the at least one LSM and the FCS device unit;
    graphically depicting results from the scanning process and creating images from the at least one LSM in correlation with FCS data; and
    determining and selecting measurement location for the analysis of molecular interaction in the at least two dimensions.

7. The method according to claim 6, wherein the preceding method steps are carried out for a plurality of specimen points which are preselected automatically and/or manually.

8. The method according to claim 6, further comprising the step of initiating an FCS measurement when the scanner is stopped during the scanner process.

* * * * *